(12) United States Patent
Dener

(10) Patent No.: US 8,143,448 B2
(45) Date of Patent: *Mar. 27, 2012

(54) PROCESS FOR THE PREPARATION OF (3S)-3-AMINO-N-CYCLOPROPYL-2-HYDROXYALKANAMIDE DERIVATIVES

(75) Inventor: Jeffrey Dener, Millbrae, CA (US)

(73) Assignee: ViroBay, Inc., Menlo Park, CA (US)

( * ) Notice: Subject to any disclaimer, the term of this patent is extended or adjusted under 35 U.S.C. 154(b) by 138 days.

This patent is subject to a terminal disclaimer.

(21) Appl. No.: 12/484,078

(22) Filed: Jun. 12, 2009

(65) Prior Publication Data

US 2009/0312571 A1    Dec. 17, 2009

Related U.S. Application Data

(60) Provisional application No. 61/061,566, filed on Jun. 13, 2008.

(51) Int. Cl.
*C07C 233/05* (2006.01)
(52) U.S. Cl. ........... 564/193; 564/165; 562/405; 560/43
(58) Field of Classification Search ............... 564/165, 564/193; 562/405; 560/43
See application file for complete search history.

(56) References Cited

U.S. PATENT DOCUMENTS

2007/0232527 A1    10/2007    Ghosal et al.

FOREIGN PATENT DOCUMENTS

| WO | WO 2007/022459 A2 | 2/2007 |
| WO | WO 2007/109080 A2 | 9/2007 |
| WO | WO 2007/139585 A1 | 12/2007 |
| WO | WO 2009/114633 A1 | 9/2009 |

*Primary Examiner* — Shailendra Kumar
(74) *Attorney, Agent, or Firm* — Kilpatrick Townsend & Stockton LLP

(57) ABSTRACT

The present invention relates to a process for the preparation of (2S,3S)-3-amino-N-cyclopropyl-2-hydroxyalkanamides as well as novel compounds prepared or used in the process.

27 Claims, No Drawings

PROCESS FOR THE PREPARATION OF (3S)-3-AMINO-N-CYCLOPROPYL-2-HYDROXYALKANAMIDE DERIVATIVES

CROSS-REFERENCES TO RELATED APPLICATIONS

This application claims the benefit of U.S. Ser. No. 61/061,566 filed Jun. 13, 2008, the content of which is incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

The present invention relates to a process for the preparation of (2S,3S)-3-amino-N-cyclopropyl-2-hydroxyalkanamide derivatives, which are intermediates useful in the synthesis of serine and cysteine protease inhibitors. In particular, the process is suitable for large scale synthesis of (2S,3S)-3-amino-N-cyclopropyl-2-hydroxypentanamide and (2S,3S)-3-amino-N-cyclopropyl-2-hydroxyhexanamide.

BACKGROUND

Hepatitis C virus (HCV) is a (+)-sense single-stranded RNA virus that is a major cause of non-A, non-B hepatitis worldwide. A large percentage of people infected with HCV develop chronic liver disease. This chronic hepatitis C infection, in turn, puts them at high risk for developing serious liver diseases such as liver cirrhosis, hepatocellular carcinoma and terminal liver disease leading to death.

Compounds having an (S)—N-cyclopropyl-2-oxo-3-(amino)alkanamide group, for example an (S)—N-cyclopropyl-2-oxo-3-(amino)hexanamide group (or (S)-3-amino-N-cyclopropyl-2-oxohexanamide) have been shown to be useful for the treatment of hepatitis C and related disorders. See, for example, U.S. Patent Application 2007/0054864, the complete disclosure of which is hereby incorporated by reference. Accordingly, it would be desirable to have a facile synthesis of common intermediates useful in the preparation of such compounds, particularly a synthesis suitable for large scale preparation of this and similar intermediates.

SUMMARY OF THE INVENTION

In one aspect, this invention is directed to a process for the preparation of (2S,3S)-3-amino-N-cyclopropyl-2-hydroxyalkanamide derivatives, comprising:
contacting a (2S,3S)—N-cyclopropyl-3-(dibenzylamino)-2-hydroxyalkanamide derivative with hydrogen in the presence of a suitable catalyst. In one embodiment, the dibenzylaminoamide derivative is (2S,3S)—N-cyclopropyl-3-(dibenzylamino)-2-hydroxyhexanamide or (2S,3S)—N-cyclopropyl-3-(dibenzylamino)-2-hydroxypentanamide, the catalyst is a palladium catalyst, for example palladium (II) hydroxide or palladium on carbon, and the reaction is carried out in an inert solvent, typically methanol or ethanol.

In a second aspect, the invention is directed to a process for the preparation of (2S,3S)—N-cyclopropyl-3-(dibenzylamino)-2-hydroxyalkanamide derivatives, comprising contacting a (2S,3S)-3-(dibenzylamino)-2-acetoxyalkanamide derivative with a base, typically aqueous sodium hydroxide, in an inert solvent, typically methanol. In one embodiment, the alkanamide is (2S,3S)-1-(cyclopropylamino)-3-(dibenzylamino)-1-oxohexan-2-yl acetate or (2S,3S)-1-(cyclopropylamino)-3-(dibenzylamino)-1-oxopentan-2-yl acetate.

In a third aspect, the invention is directed to a process for the preparation of (2S,3S)-1-(cyclopropylamino)-3-(dibenzylamino)-1-oxoalkan-2-yl acetate derivatives, comprising contacting an (S)-2-(dibenzylamino)alkanal derivative with cyclopropylisocyanide (also known as cyclopropylisonitrile) in the presence of acetic acid in an inert solvent, typically methylene chloride. In one embodiment the (S)-2-(dibenzylamino)alkanal derivative is (S)-2-(dibenzylamino)pentanal or (S)-2-(dibenzylamino)butanal.

In a fourth aspect, the invention is directed toward a process for the preparation of (S)-2-(dibenzylamino)alkanal derivative, comprising:
contacting an (S)-2-(dibenzylamino)-N-methoxy-N-methylalkanamide derivative with a reducing agent. In one embodiment, the (S)-2-(dibenzylamino)-N-methoxy-N-methylalkanamide derivative is (S)-2-(dibenzylamino)-N-methoxy-N-methylhexanamide or (S)-2-(dibenzylamino)-N-methoxy-N-methylpentanamide, the reducing agent is lithium aluminum hydride, and the reaction is typically carried out in tetrahydrofuran.

In a fifth aspect, the invention is directed toward a process for the preparation of (S)-2-(dibenzylamino)-N-methoxy-N-methylalkanamide derivatives, comprising:
a) contacting an (S)-2-aminoalkanoic acid with excess benzyl halide in the presence of a base;
b) contacting the tribenzyl compound thus formed with a base, to hydrolyze to the dibenzyl acid (S)-2-(dibenzylamino)alkanoic acid; and
c) contacting the (S)-2-(dibenzylamino)alkanoic acid with reagents suitable for amide formation, for example 1-ethyl-3-(3'-dimethylaminopropyl)-carbodiimide and 1-hydroxybenzotriazole, and contacting the complex thus formed with N,O-dimethylhydroxylamine in the presence of a tertiary base.

In step a), the acid is typically (S)-2-aminopentanoic acid or (S)-2-aminobutanoic acid, the base is typically a mixture of sodium hydroxide and potassium carbonate, or optionally potassium carbonate alone, and the reaction is carried out in an aqueous environment or ethanol. Typically, the benzyl halide is benzyl chloride or benzyl bromide.

In step b), the base is typically sodium hydroxide or lithium hydroxide, and the reaction is carried out in an aqueous environment in the presence of methanol or tetrahydrofuran.

In step c), typically the tertiary base is N-methylmorpholine, and the reaction is carried out in an inert solvent, typically methylene chloride.

In a sixth aspect, the invention is directed to a process for the preparation of (2S,3S)-3-amino-N-cyclopropyl-2-hydroxyhexanamide, comprising:
a) contacting L-norvaline ((S)-2-aminopentanoic acid) with excess benzyl halide in the presence of a base;
b) contacting the tribenzyl compound thus formed ((S)-benzyl-2-(dibenzylamino)pentanoate) with a base, to hydrolyze to the acid (S)-2-(dibenzylamino)pentanoic acid;

c) contacting the (S)-2-(dibenzylamino)pentanoic acid thus formed with reagents suitable for amide formation, for example 1-ethyl-3-(3'-dimethylaminopropyl)-carbodiimide and 1-hydroxybenzotriazole, and contacting the complex thus formed with N,O-dimethylhydroxylamine in the presence of a tertiary base;
d) contacting the (S)-2-(dibenzylamino)-N-methoxy-N-methylpentanamide thus formed with a reducing agent, typically lithium aluminum hydride in tetrahydrofuran;
e) contacting the (S)-2-(dibenzylamino)pentanal thus formed with cyclopropylisocyanide in an inert solvent; typically methylene chloride;
f) contacting the (2S,3S)-3-(dibenzylamino)-2-acetoxyhexanamide derivative with a base, typically aqueous sodium hydroxide, in an inert solvent, typically methanol;
g) contacting the (2S,3S)—N-cyclopropyl-3-(dibenzylamino)-2-hydroxyhexanamide thus formed with hydrogen in the presence of a suitable catalyst, typically palladium hydroxide or palladium on carbon.

In a seventh aspect, the invention relates to intermediates formed in the process, for example (S)-benzyl-2-(dibenzylamino)butanoate, (S)-benzyl 2-(dibenzylamino)-pentanoate, (S)-benzyl 3-cyclobutyl-2-(dibenzylamino)propanoate, (S)-2-(dibenzylamino)butanoic acid, (S)-benzyl 2-(dibenzylamino)pentanoic acid, (S)-benzyl 3-cyclobutyl-2-(dibenzylamino)propanoic acid, (S)-2-(dibenzylamino)-N-methoxy-N-methylbutanamide, (S)-2-(dibenzylamino)-N-methoxy-N-methylpentanamide, (S)-3-cyclobutyl-2-(dibenzylamino)-N-methoxy-N-methylpropanamide, (S)-2-(dibenzylamino)butanal, (S)-2-(dibenzylamino)pentanal, (S)-3-cyclobutyl-2-(dibenzylamino)propanal, (2S,3S)-1-(cyclopropylamino)-3-(dibenzylamino)-1-oxopentan-2-yl acetate, (2S,3S)-1-(cyclopropylamino)-3-(dibenzylamino)-1-oxohexan-2-yl acetate, (2S,3S)-4-cyclobutyl-1-(cyclopropylamino)-3-(dibenzylamino)-1-oxobutan-2-yl acetate, (2S,3S)-4-cyclobutyl-N-cyclopropyl-3-(dibenzylamino)-2-hydroxybutanamide, (2S,3S)—N-cyclopropyl-3-(dibenzylamino)-2-hydroxypentanamide, and (2S,3S)-4-cyclobutyl-N-cyclopropyl-3-(dibenzylamino)-2-hydroxybutanamide.

BRIEF DESCRIPTION OF THE DRAWINGS

Not Applicable

DETAILED DESCRIPTION OF THE INVENTION

The present invention provides processes for the preparation of a key intermediate in the production of HCV inhibitors.

Previously, one method used in the synthesis of HCV inhibitors containing an (S)—N-cyclopropyl-2-oxo-3-(propylamino)hexanamide group has proceeded through an intermediate of formula (f), which has a t-BOC protecting group, which is then removed to provide the free amine (g). See, for example, U.S. Patent Application 2007/0054864, the complete disclosure of which is hereby incorporated by reference. The intermediates (f) and (g) were prepared as shown below.

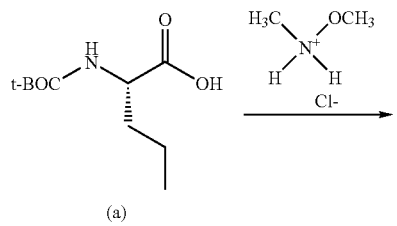

(a)

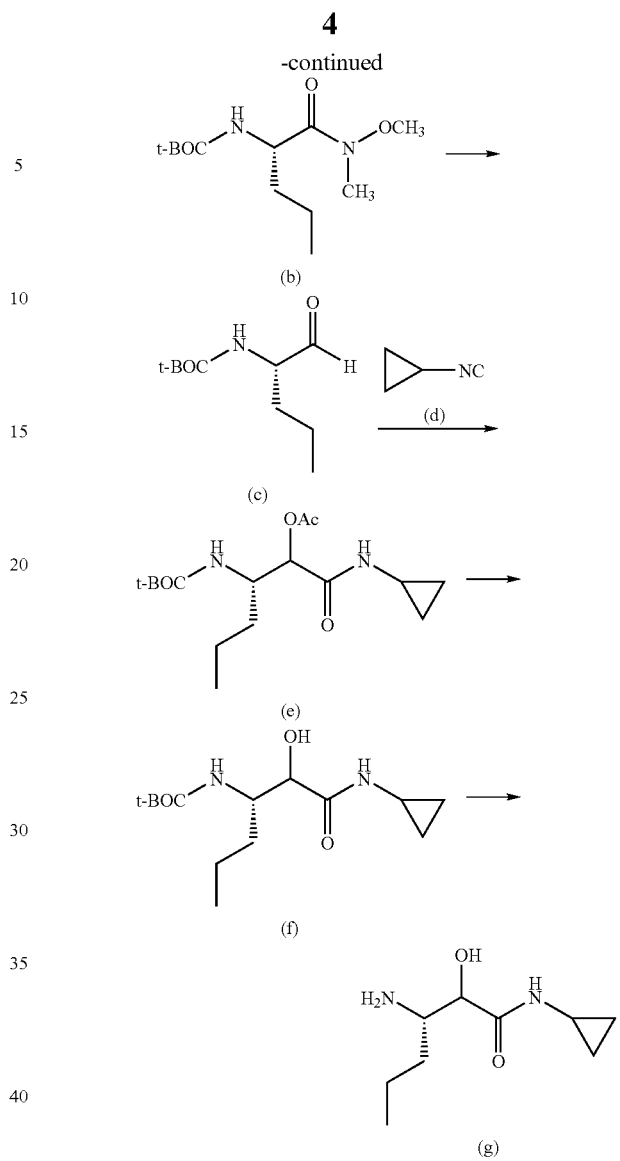

where t-BOC is t-butoxycarbonyl

The compound of formula (f) is deprotected to the free amine (g) by treatment with hydrochloric acid. Subsequent treatment of the free amine (g), with an appropriate carboxylic acid under conditions suitable for amide formation, and oxidation of the hydroxyl group of the product thus formed provides an HCV inhibitor with an (S)—N-cyclopropyl-2-oxo-3-(prop-1-en-2-ylamino)hexanamide group.

The process for the preparation of (g), shown above, has several drawbacks. For example, the protected aldehyde (c) is unstable, and cannot be stored at room temperature for any length of time. Additionally, the compound of formula (e) is produced as a mixture of diastereomers, which creates difficulties in the large scale purification of such a compound.

Accordingly, a more convenient and efficient process is desired for the preparation of HCV inhibitors containing an (S)—N-cyclopropyl-2-oxo-3-(propylamino)hexanamide group and related compounds, which is useful for large scale synthesis. Such a process is outlined in Reaction Scheme I. Bn represents a benzyl group (phenylmethylene), R is alkyl of 1-8 carbon atoms optionally substituted by cycloalkyl of 3-8 carbon atoms, for example methyl, ethyl, n-propyl, isopropyl, n-butyl, isobutyl, tert-butyl, pentyl, hexyl, cyclopropylmethyl, cyclopropylethyl, cyclobutylmethyl, cyclobutylethyl, cyclobutylpropyl, cyclopentylethyl, cyclohexylpropyl, and the like. Inert solvent means a solvent that is inert to the conditions of the reaction being described.

"Alkyl" means a straight or branched, saturated aliphatic radical containing one to eight carbon atoms, optionally substituted by cycloalkyl of 3-8 carbon atoms, e.g., methyl, ethyl, propyl, isopropyl, butyl, sec-butyl, isobutyl, tert-butyl, cyclopropylmethyl, cyclopropylethyl, cyclobutylmethyl, cyclobutylmethyl, and the like.

"Cycloalkyl" refers to a monovalent saturated monocyclic ring containing three to eight ring carbon atoms e.g., cyclopropyl, cyclobutyl, cyclopentyl, cyclohexyl, and the like.

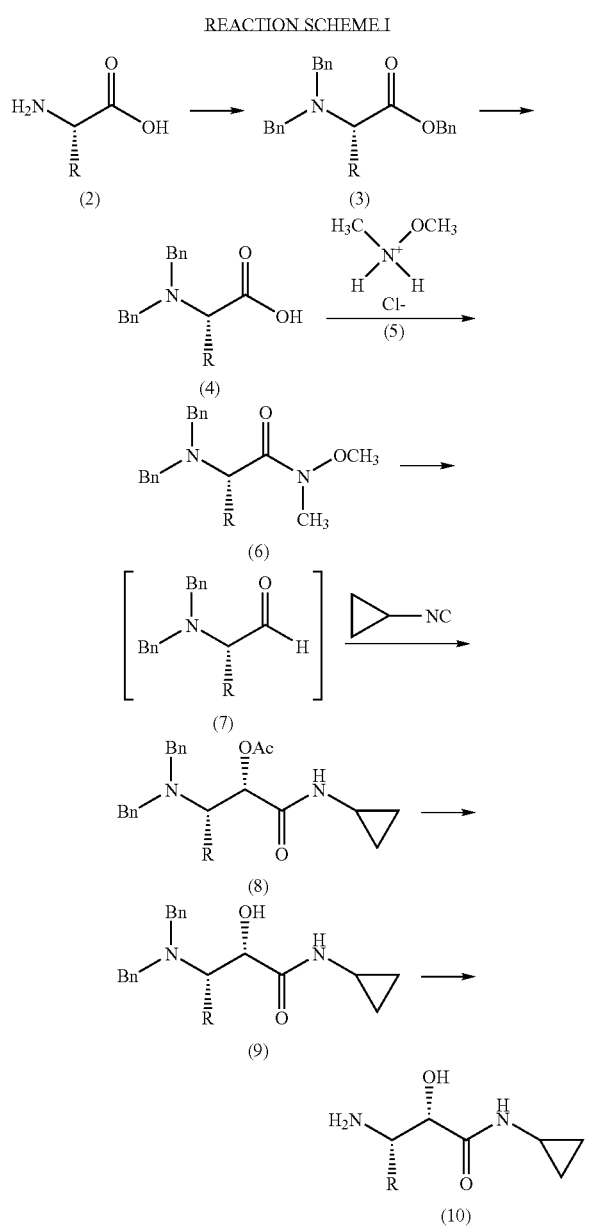

where Bn is benzyl and R is alkyl as defined above

There are several advantages of such a process. The use of benzyl groups as protecting groups provides intermediates that are stable, and, in the case of compounds (4), (8), and (9) provides compounds that are solids, which are much easier to purify on a large scale by standard techniques, for example by recrystallization. The use of benzyl groups also provides a chromophore that makes it easier to follow the progress of the reactions and their end points, and to better analyze the intermediates for chemical and stereochemical purity, whereas the t-BOC group does not. Additionally, the compound of formula (8) is produced essentially as a single diastereomer, and thus much easier to characterize and purify on a large scale; the same advantage is provided for all subsequent steps. Also, the intermediate of formula (9) is a stable solid, and thus serves as a purification control point, for example by slurrying with a mixture of ethyl acetate and hexane; and is easily deprotected (by hydrogenation) to provide the free amine of formula (10). This pure amine is then reacted with an appropriate carboxylic acid under conditions suitable for amide formation, as explained above, as a first step in the synthesis of an HCV inhibitor with an (S)—N-cyclopropyl-2-oxo-3-(propylamino)alkanamide group. By contrast, syntheses that rely upon removal of the t-BOC group under highly acidic conditions tend to degrade the product, for example by hydrolysis of the cyclopropyl amide, particularly when extended reaction times are required.

Step 1—Preparation of a Compound of Formula (3)

To a mixture of bases, typically sodium hydroxide and potassium carbonate, in aqueous solution, is added an (S)-2-aminoalkanoic acid, for example (S)-2-aminopentanoic acid (L-norvaline). The reaction is initially carried out at a temperature of about 0-5° C., then at about 85-95° C. To the solution thus formed is added a benzyl halide, typically benzyl bromide or benzyl chloride, and the mixture maintained at about 85-95° C. When the reaction is substantially complete, the product of formula (3) is isolated by conventional means, for example by extraction with an inert organic solvent, separation of the organic solvent layer, and removal of the solvent under reduced pressure, to provide an (S)-benzyl-2-(dibenzylamino)alkanoate derivative (3), for example(S)-benzyl-2-(dibenzylamino)pentanoate. The product can be used in the next step with no further purification.

Step 2—Preparation of a Compound of Formula (4)

The compound of formula (3) dissolved in a protic solvent, for example methanol, is contacted with an aqueous solution of a base, typically sodium hydroxide, at about 0-5° C. The reaction is conducted at about reflux temperature for about 6-24 hours. When the reaction is substantially complete, the product of formula (4) is isolated by conventional means, for example by extracting impurities with an inert solvent, acidifying the aqueous layer, extracting product with an inert solvent, removing solvent under reduced pressure, to provide an (S)-2-(dibenzylamino)alkanoic acid of formula (4).

Step 3—Preparation of a Compound of Formula (6)

The compound of formula (4) is dissolved in an inert solvent, for example dichloromethane at about 0-5° C., and reagents that promote amide formation are added, typically a mixture of 1-ethyl-3-(3'-dimethylaminopropyl)carbodiimide (EDCI, typically available as the hydrochloride salt) and 1-hydroxybenzotriazole (HOBT). The reaction is conducted at about room temperature for about 6-24 hours, then cooled to about 0-5° C. and then a tertiary base added, typically N-methylmorpholine, followed by N,O-dimethylhydroxylamine hydrochloride (5). The reaction mixture is maintained at about room temperature for about 12-24 hours. When the reaction is substantially complete, the product of formula (6) is isolated by conventional means, to provide an (S)-2-(dibenzylamino)-N-methoxy-N-methylalkanamide of formula (6).

Step 4—Preparation of a Compound of Formula (7)

To a solution of a reducing agent, typically lithium aluminum hydride, in an inert solvent, typically tetrahydrofuran, at about −20- to −30° C., is added the compound of formula (6), an (S)-2-(dibenzylamino)-N-methoxy-N-methylalkanamide, in an inert solvent, typically tetrahydrofuran. When the reaction is substantially complete, the product of formula (7) is isolated by conventional means, to provide an (S)-2-(dibenzylamino)alkanal of formula (7), which is used without purification in the next step.

Step 5—Preparation of a Compound of Formula (8)

The crude compound of formula (7) is dissolved in an inert solvent, for example methylene chloride, cooled to about 0-5° C., and cyclopropylisocyanide added, followed by acetic acid. The reaction temperature is allowed to warm to about 25-30° C. for 40-90 minutes, and stirred for about 16-24 hours at that temperature. When the reaction is substantially complete, the acid is neutralized, for example with sodium bicarbonate, and the product of formula (8) is isolated by conventional means, to provide a (2S,3S)-3-(dibenzylamino)-2-acetoxyalkanenitrile of formula (8).

Step 6—Preparation of a Compound of Formula (9)

The product of formula (8) is hydrolyzed under basic conditions, for example by reaction with an aqueous base, typically aqueous sodium hydroxide, in a protic solvent, typically methanol. The reaction is initially conducted at a temperature of about 0-5° C., and then allowed to warm to about 25-30° C., for about 16-24 hours. When the reaction is substantially complete, the product of formula (9) is isolated by conventional means, to provide a crude (2S,3S)—N-cyclopropyl-3-(dibenzylamino)-2-hydroxyalkanamide of formula (9). The absolute stereochemistry of this diastereomer where R is n-propyl has been shown to be the anti-isomer (2S,3S)-configuration, by conversion of the compound of formula (14) to a cyclic derivative (the oxazolidinone) with phosgene, and has been shown to be up to 99% pure as a single isomer.

Step 7—Preparation of the Compound of Formula (10)

The compound of formula (9) is dissolved in an inert solvent, for example methanol, and a metal catalyst added, for example a palladium metal catalyst, typically palladium(II) hydroxide or palladium on carbon, at about room temperature, and the mixture stirred under hydrogen at about 40-60 psi. When the reaction is substantially complete, the product is isolated by conventional means, typically by filtering the catalyst off and removing the solvent under reduced pressure, to provide a (2S,3S)-3-amino-N-cyclopropyl-2-hydroxyalkanamide, a compound of formula (10).

One utility of the compound of formula (10) is shown in Reaction Scheme II.

REACTION SCHEME II

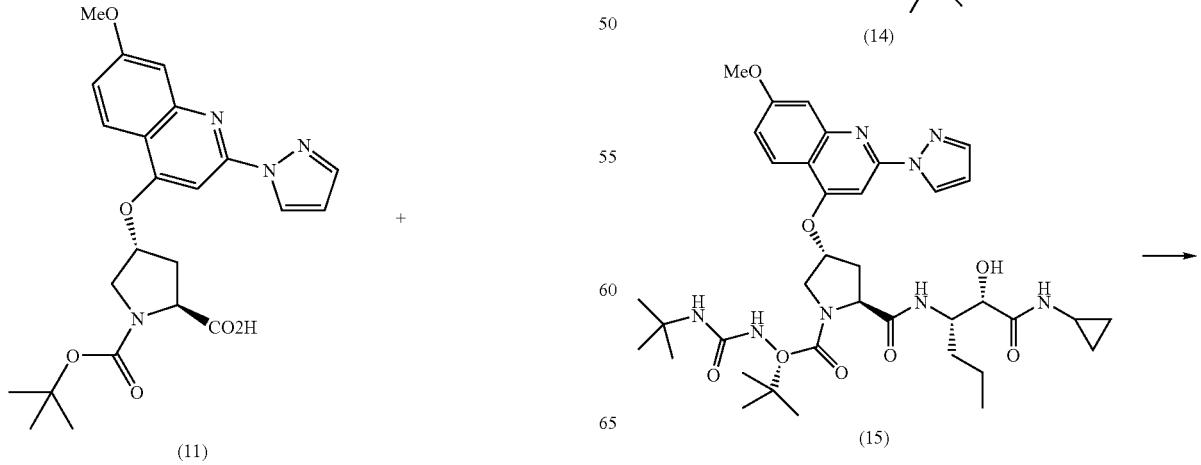

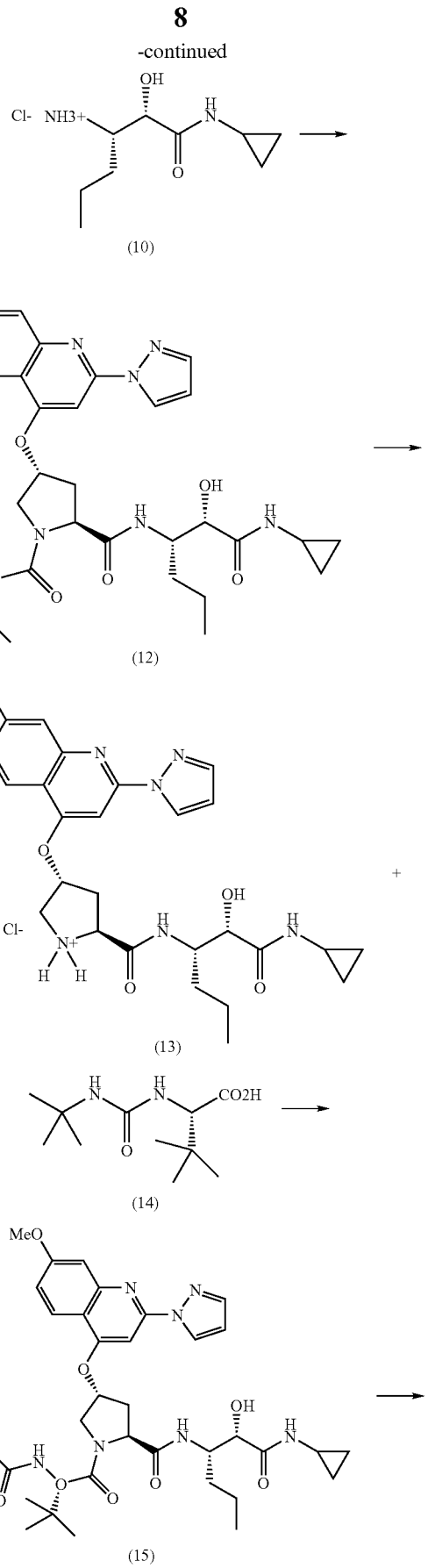

-continued

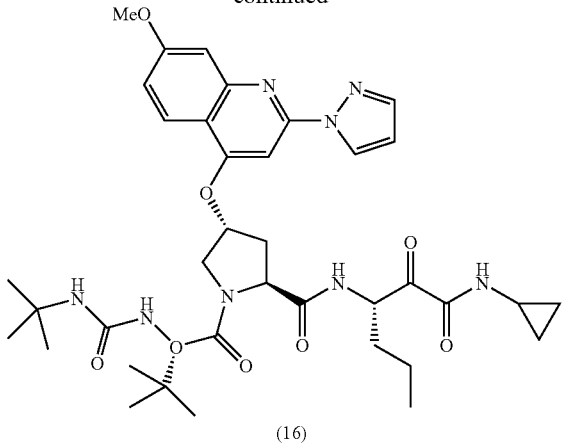

(16)

Step 1—Preparation of a Compound of Formula (12)

To a solution of the compound of formula (11) in an inert solvent, typically a mixture of dichloromethane and N,N-dimethylformamide, is added reagents that promote amide formation added, typically a mixture of 2-(1H-7-Azabenzotriazol-1-yl)-1,1,3,3-tetramethyluronium hexafluorophosphate (HATU) and a tertiary base, for example diisopropylethylamine, at about room temperature, followed by the compound of formula (10), typically as its hydrochloride salt. When the reaction is substantially complete, the product is isolated by conventional means, to provide (2S,4R)-tert-butyl 2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidine-1-carboxylate, the compound of formula (16)

Step 2—Preparation of a Compound of Formula (13)

To a solution of the compound of formula (12) in an inert solvent, for example methanol, is added dropwise a methanolic hydrochloric acid solution (typically about 10-20% by weight HCl). The reaction mixture is maintained at about room temperature for about 1-5 hours. When the reaction is substantially complete, the product is isolated by conventional means, to provide (2S,4R)-2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidinium chloride, the compound of formula (13).

Step 3—Preparation of a Compound of Formula (15)

To a solution of the compound of formula (13) in a polar solvent, typically dimethylsulfoxide, is added the compound of formula (14) and reagents that promote amide formation added, typically a mixture of 2-(1H-7-Azabenzotriazol-1-yl)-1,1,3,3-tetramethyluronium hexafluorophosphate (HATU) and a tertiary base, for example diisopropylethylamine. The reaction is conducted at about room temperature for about 1-5 hours. When the reaction is substantially complete, the product is isolated by conventional means, to provide (2S,4R)-1-((S)-2-(3-tert-butylureido)-3,3-dimethylbutanoyl)-N-((2S,3S)-1-(cyclopropylamino)-2-hydroxy-1-oxohexan-3-yl)-4-(7-methoxy-2-(1H-pyrazol-1-yl)quinolin-4-yloxy)pyrrolidine-2-carboxamide, the compound of formula (15).

As discussed above, the compound of formula (10) is synthesized as a single diastereomer [(2S,3S)-3-amino-N-cyclopropyl-2-hydroxyalkanamide], which is an advantage with respect to the ability to characterize and purify on a large scale, for example by crystallization. This advantage carries over to the compound of formula (15), which is also prepared a single diasteromer, and thus easy to purify on a large scale before the final oxidation step.

Step 4—Preparation of a Compound of Formula (16)

To a solution of the compound of formula (15) in an inert solvent, for example dichloromethane, is added Dess-Martin Periodinane reagent at about room temperature for about 1 hour. Completion of the reaction is monitored by TLC analysis. When the reaction is substantially complete, the product is isolated by conventional means, to provide (2S,4R)-1-((S)-2-(3-tert-butylureido)-3,3-dimethylbutanoyl)-N—((S)-1-(cyclopropylamino)-1,2-dioxohexan-3-yl)-4-(7-methoxy-2-(1H-pyrazol-1-yl)quinolin-4-yloxy)pyrrolidine-2-carboxamide, the compound of formula (16), a compound useful as an HCV inhibitor.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of a Compound of Formula (3)

A. Preparation of (S)-benzyl 2-(dibenzylamino)pentanoate

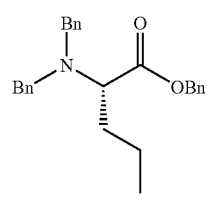

Sodium hydroxide (0.513 Kg; 12.82 moles) and potassium carbonate (1.77 Kg, 12.82 moles) were dissolved in water (7.5 L) and cooled to 0° C. The resulting solution was treated with (S)-2-aminopentanoic acid (L-norvaline, 0.75 Kg; 6.41 moles) slowly at between 0-5° C. The stirred suspension was heated at 90° C. and benzyl bromide (4.385 Kg, 25.64 moles) was added dropwise. Heating was continued for a further 12 hours at 90° C. The reaction mixture was then cooled to ambient temperature, and extracted with ethyl acetate (2×6 liters). The layers were separated and the aqueous phase extracted twice with ethyl acetate. The combined organic extracts were dried over sodium sulfate, and the solvent removed under reduced pressure to obtain 3.3 Kg of crude (S)-benzyl 2-(dibenzylamino)pentanoate, a compound of formula (3), as a brown oil. This material was used in the next reaction without further purification.

$^1$H NMR (CDCl$_3$): δ 7.42-7.18 (15H, m, Ar—H), 5.18 (2H, q, OCH$_2$Ph), 3.98-3.42 (4H, q, 2×NCH$_2$Ph), 3.38 (1H, t, CH), 1.8-1.2 (4H, m, CH$_2$), 0.79 (3H, t, CH$_3$).

LC-MS: 388 (M+H)$^+$

B. Preparation of (S)-benzyl 2-(dibenzylamino)butanoate

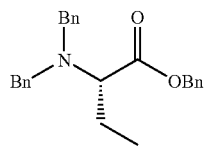

Similarly, following the procedure of Example 1A, but replacing (S)-2-aminopentanoic acid with (S)-2-aminobutanoic acid, (S)-benzyl 2-(dibenzylamino)butanoate is prepared.

C. Preparation of (S)-benzyl 3-cyclobutyl-2-(dibenzylamino)propanoate

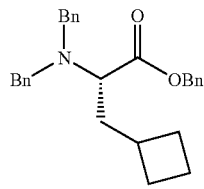

Similarly, following the procedure of Example 1A, but replacing (S)-2-aminopentanoic acid with (S)-2-amino-3-cyclobutylpropanoic acid, (S)-benzyl 3-cyclobutyl-2-(dibenzylamino)propanoate is prepared.

D. Preparation of other (S)-benzyl 2-(dibenzylamino)alkanoate Derivatives of Formula (3)

Similarly, following the procedure of Example 1A, but replacing (S)-2-aminopentanoic acid with amino acids of formula (2):

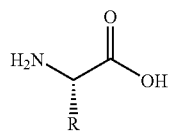

(2)

where R is as defined above, other (S)-benzyl 2-(dibenzylamino)alkanoate derivatives of formula (3) are prepared.

Example 2

Preparation of a Compound of Formula (4)

A. Preparation of (S)-2-(Dibenzylamino)pentanoic acid

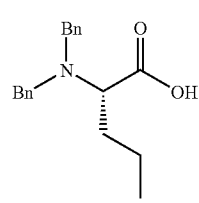

(4)

The crude (S)-benzyl 2-(dibenzylamino)pentanoate (3) (2.2 Kg) was dissolved in methanol (5.5 L). A previously prepared, cold (0-5° C.) solution of sodium hydroxide (568 g; 14.2 mol) in water (6 L) was added to the solution of (3), and the resulting mixture heated at 90° C. for 20 hours. The reaction mixture was then allowed to cool to ambient temperature, and the methanol evaporated under reduced pressure. The residue was diluted with water (25 L), and extracted with methyl t-butyl ether/hexane (1:1; 2×5 L) to remove the benzyl alcohol formed in the hydrolysis. The basic aqueous layer was acidified to pH 2 with 6M aqueous hydrochloric acid (4 L), then extracted with ethyl acetate (2×8 L). The combined organic extracts were dried over sodium sulfate and the solvent removed under reduced pressure, to afford a semi solid, which was washed with hexanes (8 L) to provide 1.12 Kg of (S)-2-(dibenzylamino)pentanoic acid, a compound of formula (4), as a white solid.

$^1$H-NMR (CDCl$_3$) 7.42-7.2 (10H, m, Ph-H), 3.75 (4H, s, NCH$_2$Ph), 3.38 (1H, t, CH), 1.8 (2H, m, CH$_2$), 1.45 (2H, m, CH$_2$), 0.79 (3H, t, CH$_3$).

LC-MS: 298 (M+H)$^+$

B. Preparation of (S)-benzyl 2-(dibenzylamino)butanoic acid

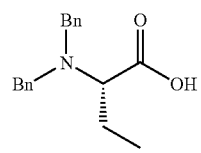

Similarly, following the procedure of Example 2A, but replacing (S)-benzyl 2-(dibenzylamino)pentanoate with (S)-benzyl 2-(dibenzylamino)butanoate, (S)-2-(dibenzylamino) butanoic acid is prepared.

C. Preparation of (S)-3-cyclobutyl-2-(dibenzylamino)propanoic acid

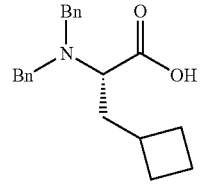

Similarly, following the procedure of Example 2A, but replacing (S)-benzyl 2-(dibenzylamino)pentanoate with (S)-benzyl 3-cyclobutyl-2-(dibenzylamino)propanoate, (S)-2-(dibenzylamino)butanoic acid is prepared.

D. Preparation of other (S)-benzyl 2-(dibenzylamino)alkanoic acids of Formula (4)

Similarly, following the procedure of Example 2A, but replacing (S)-benzyl 2-(dibenzylamino)pentanoate with other compounds of formula (3):

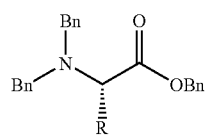

(3)

where R is alkyl as defined above, other (S)-benzyl 2-(dibenzylamino)alkanoic acids of formula (4) are prepared.

Example 3

Preparation of a Compound of Formula (6)

A. Preparation of (S)-2-(Dibenzylamino)-N-methoxy-N-methylpentanamide

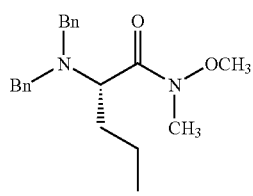

(S)-2-(dibenzylamino)pentanoic acid (1.57 Kg; 5.286 mol) was dissolved in dry dichloromethane (9.42 L) under a nitrogen atmosphere and cooled to 0-5° C. The resulting solution was treated with N-hydroxybenzotriazole (HOBt; 928 g; 6.875 mol) followed by 1-ethyl-3-(3'-dimethylaminopropyl)carbodiimide hydrochloride (EDCI, 1.51 Kg; 7.931 mol;) at 0-5° C. The reaction mixture was stirred for 3 hours at ambient temperature, then treated with N-methylmorpholine (NMM; 1.62 Kg; 16.07 mol) followed by N,O-dimethylhydroxylamine hydrochloride (1.29 Kg; 13.22 mol) at 0° C. The reaction mixture was stirred at ambient temperature for 15 hours, then water (2.5 L) added, and the mixture stirred for 10 minutes. The organic layer was separated, washed with 1% aqueous hydrochloric acid, followed by saturated aqueous sodium bicarbonate, then brine solution. The organic phase was dried over sodium sulfate, filtered and concentrated under reduced pressure to provide (S)-2-(dibenzylamino)-N-methoxy-N-methylpentanamide, a compound of formula (6), as a syrupy oil.

$^1$H-NMR (CDCl$_3$) 7.42-7.15 (10H, m, Ph-H), 3.6-3.4 (5H, m, NCH$_2$Ph+CH), 3.23-3.0 (6H, 2s, NMe+OMe), 1.4-1.8 (4H, m, CH$_2$), 0.85 (3H, t, CH$_3$).

LC-MS: 340 (M+H)$^+$

B. Preparation of (S)-2-(dibenzylamino)-N-methoxy-N-methylbutanamide

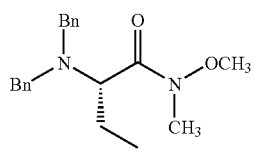

Similarly, following the procedure of Example 3A, but replacing (S)-2-(dibenzylamino)pentanoic acid with (S)-2-(dibenzylamino)butanoic acid, (S)-2-(dibenzylamino)-N-methoxy-N-methylbutanamide is prepared.

C. Preparation of (S)-3-cyclobutyl-2-(dibenzylamino)-N-methoxy-N-methylpropanamide

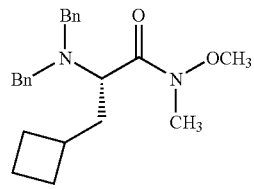

Similarly, following the procedure of Example 3A, but replacing (S)-2-(dibenzylamino)pentanoic acid with (S)-2-(dibenzylamino)butanoic acid, (S)-3-cyclobutyl-2-(dibenzylamino)-N-methoxy-N-methylpropanamide is prepared.

D. Preparation of other (S)-2-(dibenzylamino)-N-methoxy-N-methyalkanamides of Formula (6)

Similarly, following the procedure of Example 3A, but replacing (S)-2-(dibenzylamino)pentanoic acid with other compounds of formula (4):

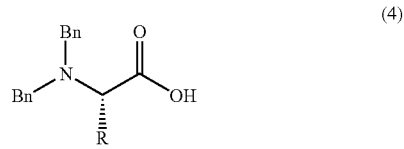

(4)

where R is alkyl as defined above, other (S)-2-(dibenzylamino)-N-methoxy-N-methylalkanamides of formula (6) are prepared.

Example 4

Preparation of a Compound of Formula (7)

A. Preparation of (S)-2-(Dibenzylamino)pentanal

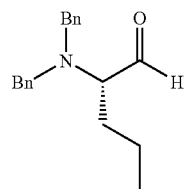

To anhydrous tetrahydrofuran (1.5 L) previously cooled to −20° C. to −30° C. was added solid lithium aluminum hydride (33.5 g; 0.882 mol; 120 mole %) slowly with stirring. A solution of (S)-2-(dibenzylamino)-N-methoxy-N-methylpentanamide (6) (250 g; 0.735 mol) in anhydrous tetrahydrofuran (1 L) at −30° C. was slowly added to the above mixture under a nitrogen atmosphere. The reaction was continued for 2 hours at −30° C., monitoring progress of the reaction by TLC analysis (ethyl acetate/hexane, 1:9). Upon completion of the reaction, the excess reagent was quenched by the dropwise addition of ethyl acetate (1 L) and ice-cold water (300 ml) at −30° C. The insoluble salts were filtered through celite, the filtrate diluted with water (3 L), and the product extracted into ethyl acetate (2 L). The combined ethyl acetate layers were washed with water (2 L), dried over sodium sulfate, filtered, and solvent removed under reduced pressure to provide (S)-2-(dibenzylamino)pentanal (7) (195 g) as a light yellow oil, which was used without purification in the next step.

¹H-NMR (CDCl₃) 9.75 (1H, s, CHO), 7.40-7.20 (10H, m, Ph-H), 3.75 (4H, q, NCH₂Ph), 3.15 (1H, t, CH), 1.80-1.20 (4H, m, CH₂), 0.85 (3H, t, CH₃)

B. Preparation of (S)-2-(dibenzylamino)butanal

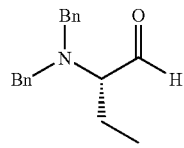

Similarly, following the procedure of Example 4A, but replacing (S)-2-(dibenzylamino)-N-methoxy-N-methylpentanamide with (S)-2-(dibenzylamino)-N-methoxy-N-methylbutanamide, (S)-2-(dibenzylamino)butanal is prepared.

C. Preparation of (S)-3-cyclobutyl-2-(dibenzylamino)propanal

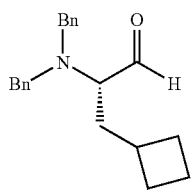

Similarly, following the procedure of Example 4A, but replacing (S)-2-(dibenzylamino)-N-methoxy-N-methylpentanamide with (S)-3-cyclobutyl-2-(dibenzylamino)-N-methoxy-N-methylpropanamide, (S)-3-cyclobutyl-2-(dibenzylamino)propanal is prepared.

D. Preparation of other (S)-2-(dibenzylamino)alkanals of Formula (7)

Similarly, following the procedure of Example 4A, but replacing (S)-2-(dibenzylamino)-N-methoxy-N-methylpentanamide with other compounds of formula (6):

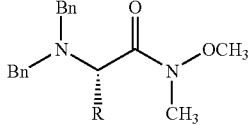

(6)

where R is alkyl as defined above, other (S)-2-(dibenzylamino)alkanals of formula (7) are prepared.

Example 5

Preparation of a Compound of Formula (8)

A. Preparation of (2S,3S)-1-(cyclopropylamino)-3-(dibenzylamino)-1-oxohexan-2-yl acetate

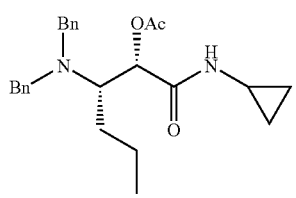

To a cooled (0-5° C.) solution of (S)-2-(dibenzylamino)pentanal in dichloromethane (210 mL) was added cyclopropylisonitrile followed by acetic acid at 0-5° C. The reaction mixture temperature was raised to 25-30° C. over 40-60 minutes, and stirred for 16-18 hours at 25-30° C. Progress of the reaction was monitored by TLC analysis. When the reaction was complete, the mixture was cooled to 0-5° C., and saturated sodium bicarbonate solution (200 mL) was added. The organic layer was separated and the aqueous layer was extracted with dichloromethane twice. The combined organic layers were washed with water (1×200 mL), brine (1×200 mL), dried over anhydrous sodium sulfate, and concentrated under reduced pressure. The crude product thus obtained was slurried in hexane (150 mL) and stirred for one hour at 25-35° C. The slurry was filtered and the solid washed with hexane and dried under reduced pressure to provide 17.0 g of (2S,3S)-1-(cyclopropylamino)-3-(dibenzylamino)-1-oxohexan-2-yl acetate as a white solid.

B. Preparation of (2S,3S)-1-(cyclopropylamino)-3-(dibenzylamino)-1-oxohexan-2-yl acetate

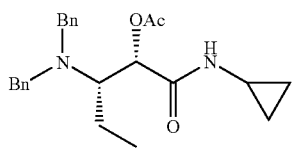

Similarly, following the procedure of Example 5A, but replacing (S)-2-(dibenzylamino)pentanal with (S)-2-(dibenzylamino)butanal, (2S,3S)-1-(cyclopropylamino)-3-(dibenzylamino)-1-oxopentan-2-yl acetate is prepared.

C. Preparation of (2S,3S)-4-cyclobutyl-1-(cyclopropylamino)-3-(dibenzylamino)-1-oxobutan-2-yl acetate

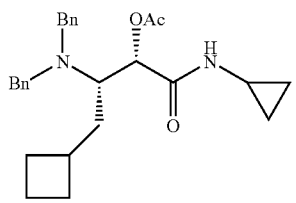

Similarly, following the procedure of Example 5A, but replacing (S)-2-(dibenzylamino)pentanal with (S)-3-cyclobutyl-2-(dibenzylamino)propanal, (2S,3S)-4-cyclobutyl-1-(cyclopropylamino)-3-(dibenzylamino)-1-oxobutan-2-yl acetate is prepared.

D. Preparation of other (2S,3S)-1-(cyclopropylamino)-3-(dibenzylamino)-1-oxoalkan-2-yl acetates of Formula (8)

Similarly, following the procedure of Example 5A, but replacing (S)-2-(dibenzylamino)pentanal with other compounds of formula (7):

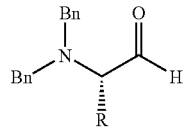

Example 6

Preparation of a Compound of Formula (9)

A. Preparation of (2S,3S)—N-cyclopropyl-3-(dibenzylamino)-2-hydroxyhexanamide

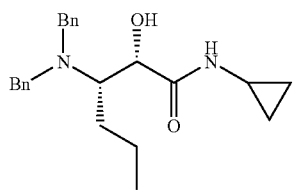

(2S,3S)-1-(cyclopropylamino)-3-(dibenzylamino)-1-oxohexan-2-yl acetate (17 g) was dissolved in methanol (120 mL) at room temperature and the resulting solution cooled to 0-5° C. To this solution was added a previously prepared 1.1-M solution of sodium hydroxide by dissolving solid NaOH (2.49 g) in water (55 mL), which was then added to the reaction mixture at 0-5° C. The reaction was warmed to room temperature (25-30° C.) and stirred at this temperature for 16-18 hours. The reaction mixture was monitored by TLC for the disappearance of starting material. Once TLC indicated that the reaction was complete, the solvent was removed by distillation under reduced pressure, keeping the temperature below 45° C. Ethyl acetate (2.5 L) was added and the resulting solution was stirred for 20-30 minutes. The organic layer was washed with water (500 mL), followed by an aqueous solution of sodium chloride (brine; 300 mL). The organic layer was dried (sodium sulfate), filtered and the filtrate was concentrated under reduced pressure, keeping the temperature below 40° C. n-Hexane (100 mL) was added, and the slurry was stirred for one hour at 25-30° C. The resulting solid was filtered off, then dried under reduced pressure to provide (2S,3S)—N-cyclopropyl-3-(dibenzylamino)-2-hydroxyhexanamide (11.3 g) as a white solid.

B. Preparation of (2S,3S)—N-cyclopropyl-3-(dibenzylamino)-2-hydroxypentanamide

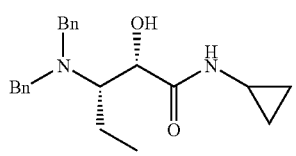

Similarly, following the procedure of Example 6A, but replacing (2S,3S)-1-(cyclopropylamino)-3-(dibenzylamino)-1-oxohexan-2-yl acetate with (2S,3S)-1-(cyclopropylamino)-3-(dibenzylamino)-1-oxopentan-2-yl acetate, (2S,3S)—N-cyclopropyl-3-(dibenzylamino)-2-hydroxypentanamide is prepared.

C. Preparation of (2S,3S)-4-cyclobutyl-N-cyclopropyl-3-(dibenzylamino)-2-hydroxybutanamide

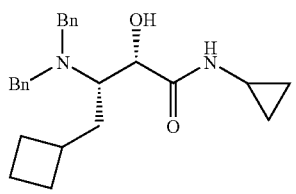

Similarly, following the procedure of Example 6A, but replacing (2S,3S)-1-(cyclopropylamino)-3-(dibenzylamino)-1-oxohexan-2-yl acetate with (2S,3S)-4-cyclobutyl-1-(cyclopropylamino)-3-(dibenzylamino)-1-oxobutan-2-yl acetate, (2S,3S)-4-cyclobutyl-N-cyclopropyl-3-(dibenzylamino)-2-hydroxybutanamide is prepared.

D. Preparation of other (2S,3S)—N-cyclopropyl-3-(dibenzylamino)-2-hydroxyalkanamides of Formula (9)

Similarly, following the procedure of Example 6A, but replacing (2S,3S)-1-(cyclopropylamino)-3-(dibenzylamino)-1-oxohexan-2-yl acetate with other compounds of formula (8):

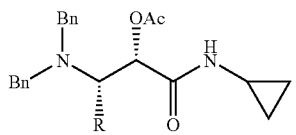

where R is alkyl as defined above, other (2S,3S)—N-cyclopropyl-3-(dibenzylamino)-2-hydroxyalkanamides of formula (9) are prepared.

Example 7

Preparation of a Compound of Formula (10)

A. Preparation of (2S,3S)-3-amino-N-cyclopropyl-2-hydroxyhexanamide

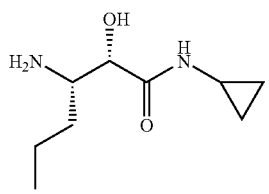

To a solution of (2S,3S)—N-cyclopropyl-3-(dibenzylamino)-2-hydroxyhexanamide (35.0 g) in methanol (350 mL) was carefully added palladium hydroxide on carbon (20% Pd(OH)$_2$/C, 7.0 g), and the mixture was stirred under hydrogen at 50 psi for 2 hours. The mixture was filtered through Celite, and washed with methanol (150 mL). The solvent was evaporated under reduced pressure, to provide a light yellow solid, which was further washed with hexanes (2×75 mL), to give (2S,3S)-3-amino-N-cyclopropyl-2-hydroxyhexanamide (16.4 g).

$^1$H NMR: $^1$H-NMR (CDCl$_3$) 7.58 (1H, bd, —CONH), 3.81 (1H, bd, —OH), 3.12 (1H, m, —CH), 2.78 (1H, m, —CH), 2.21 (2H, bd, NH$_2$), 1.20-1.58 (4H, m, —CH$_2$), 0.92 (3H, t, —CH$_3$), 0.81 (2H, m, CH$_2$ of cyclopropane), 0.51 (2H, CH$_2$ of cyclopropane).

B. Preparation of (2S,3S)-3-amino-N-cyclopropyl-2-hydroxypentanamide

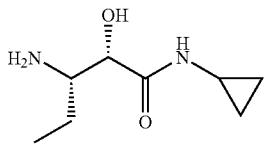

Similarly, following the procedure of Example 9A, but replacing (2S,3S)—N-cyclopropyl-3-(dibenzylamino)-2-hydroxyhexanamide with (2S,3S)—N-cyclopropyl-3-(dibenzylamino)-2-hydroxypentanamide, (2S,3S)-3-amino-N-cyclopropyl-2-hydroxypentanamide is prepared.

C. Preparation of (2S,3S)-3-amino-4-cyclobutyl-N-cyclopropyl-2-hydroxybutanamide

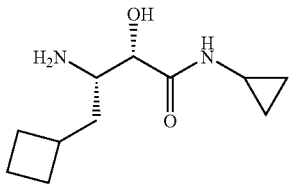

Similarly, following the procedure of Example 9A, but replacing (2S,3S)—N-cyclopropyl-3-(dibenzylamino)-2-hydroxyhexanamide with (2S,3S)-4-cyclobutyl-N-cyclopropyl-3-(dibenzylamino)-2-hydroxybutanamide, (2S,3S)-3-amino-4-cyclobutyl-N-cyclopropyl-2-hydroxybutanamide is prepared.

D. Preparation of other (2S,3S)-3-amino-N-cyclopropyl-2-hydroxyalkanamides of Formula (10)

Similarly, following the procedure of Example 9A, but replacing (2S,3S)—N-cyclopropyl-3-(dibenzylamino)-2-hydroxyhexanamide with other compounds of formula (9):

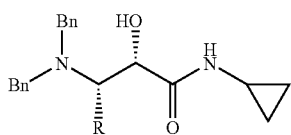
(13)

where R is alkyl as defined above, other (2S,3S)-3-amino-N-cyclopropyl-2-hydroxyalkanamides of formula (10) are prepared.

Determination of the Absolute Stereochemistry of (2S,3S)-3-amino-N-cyclopropyl-2-hydroxyhexanamide (3S)-3-Amino-N-cyclopropyl-2-hydroxyhexanamide was converted to the corresponding oxazolidinone by reaction with triphosgene. The resulting product was analyzed by proton NMR and the stereochemistry of the product was determined by the coupling constants (J value) for the protons at C-4 and C-5 of the cyclized derivatives. Based on literature values for similar products (Tsuda, M.; Muraoka, Y.; Nagai, M.; Aoyagi, T.; Takeuchi, T. J. Antibiotics 1996, 49, 281-286, Herranz, R.; Castro-Pichel, J.; Vinuesa, S.; Garcia-López. M. T. J. Org. Chem. 1990, 55, 2232, Williams, T. M.; Crumbie, R.; Mosher, H. S. J. Org. Chem. 1985, 50, 91-97), the cis-isomer (J$_{4,5}$=8.8 Hz) was obtained exclusively from the reaction of (2S,3S)-3-amino-N-cyclopropyl-2-hydroxyhexanamide with triphosgene, indicating that the absolute configuration of (3S)-3-amino-N-cyclopropyl-2-hydroxyhexanamide was (2S,3S).

What is claimed is:

1. A process for the preparation of (2S,3S)-3-amino-N-cyclopropyl-2-hydroxyalkanamide derivatives of formula (10):

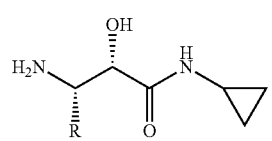
(10)

where R is alkyl of 1-6 carbon atoms optionally substituted by cycloalkyl of 3-6 carbon atoms, comprising:
contacting a (2S,3S)—N-cyclopropyl-3-(dibenzylamino)-2-hydroxyalkanamide of formula (9):

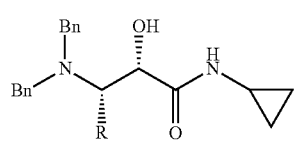
(9)

with hydrogen in the presence of a metal catalyst; wherein the (2S,3S)—N-cyclopropyl-3-(dibenzylamino)-2-hydroxyalkanamide of formula (9) is prepared by contacting a (2S,3S)—N-cyclopropyl-3-(dibenzylamino)-2-acetoxyalkanamide derivative of formula (8):

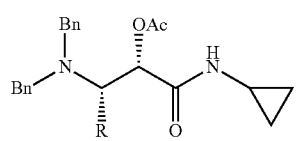
(8)

with a base.

2. The process of claim 1, wherein the catalyst is palladium (II)hydroxide, and the reaction is carried out in methanol or ethanol.

3. The process of claim 2, wherein R is ethyl, n-propyl, or cyclobutylmethyl.

4. The process of claim 1, wherein the base is aqueous sodium hydroxide in methanol and R is ethyl, n-propyl, or cyclobutylmethyl.

5. The process of claim 1, wherein the (2S,3S)—N-cyclopropyl-3-(dibenzylamino)-2-acetoxyalkanamide derivative of formula (8) is prepared by contacting an (S)-2-(dibenzylamino)alkanal derivative of formula (7):

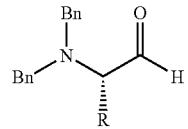
(7)

wherein R is alkyl of 1-6 carbon atoms optionally substituted by cycloalkyl of 3-6 carbon atoms; with cyclopropylisocyanide in the presence of acetic acid.

6. The process of claim 5, wherein the reaction is carried out in methylene chloride and R is ethyl, n-propyl, or cyclobutylmethyl.

7. The process of claim 5, wherein the (S)-2-(dibenzylamino)alkanal of formula (7) is prepared by contacting an (S)-2-(dibenzylamino)-N-methoxy-N-methylalkanamide of formula (6):

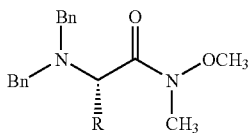

(6)

wherein R is alkyl of 1-6 carbon atoms optionally substituted by cycloalkyl of 3-6 carbon atoms; with a reducing agent.

8. The process of claim 7, wherein the reducing agent is lithium aluminum hydride, and the reaction is carried out in tetrahydrofuran, and R is ethyl, n-propyl, or cyclobutylmethyl.

9. The process of claim 7, wherein the (S)-2-(dibenzylamino)-N-methoxy-N-methylalkanamide of formula (6) is prepared by contacting an (S)-2-(dibenzylamino)alkanoic acid of formula (4):

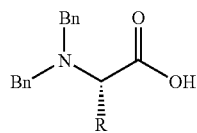

(4)

wherein R is alkyl of 1-6 carbon atoms optionally substituted by cycloalkyl of 3-6 carbon atoms; with
a) reagents suitable for amide formation in an inert solvent, followed by;
b) contacting the complex thus formed with N,O-dimethylhydroxylamine in the presence of a tertiary base.

10. The process of claim 9, wherein in step a) the reagents suitable for amide formation are 1-ethyl-3-(3'-dimethylaminopropyl)-carbodiimide and 1-hydroxybenzotriazole, and the inert solvent is dichloromethane and in step b) the tertiary base is N-methylmorpholine.

11. The process of claim 10, wherein R is ethyl, n-propyl, or cyclobutylmethyl.

12. The process of claim 9, wherein the (S)-2-(dibenzylamino)alkanoic acid of formula (4) is prepared by contacting an (S)-benzyl 2-(dibenzylamino)alkanoate of formula (3):

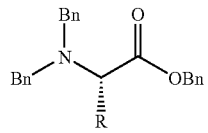

(3)

wherein R is alkyl of 1-6 carbon atoms optionally substituted by cycloalkyl of 3-6 carbon atoms; with a base in an inert solvent.

13. The process of claim 12, wherein the base is sodium hydroxide, the inert solvent is aqueous methanol, and R is ethyl, n-propyl, or cyclobutylmethyl.

14. The process of claim 12, wherein the (S)-benzyl 2-(dibenzylamino)alkanoate of formula (3) is prepared by contacting an (S)-2-aminoalkanoic acid of formula (2):

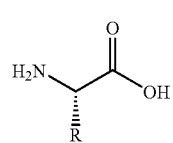

(2)

wherein R is alkyl of 1-6 carbon atoms optionally substituted by cycloalkyl of 3-6 carbon atoms; with a benzyl halide in the presence of at least one base in a solvent.

15. The process of claim 14, wherein the bases are a mixture of sodium hydroxide and potassium carbonate, the solvent is water, and the benzyl halide is benzyl chloride or benzyl bromide, and R is ethyl, n-propyl, or cyclobutylmethyl.

16. A process for the preparation of (2S,3S)-3-amino-N-cyclopropyl-2-hydroxyhexanamide:

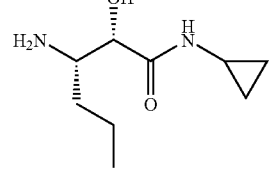

comprising:
a) contacting an (S)-2-aminopentanoic acid:

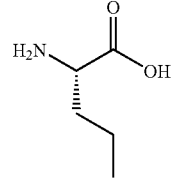

with a benzyl halide in the presence of at least one base in a solvent;
b) contacting the (S)-benzyl 2-(dibenzylamino)pentanoate thus formed with a base in an inert solvent;
c) contacting the (S)-2-(dibenzylamino)pentanoic acid thus formed with reagents suitable for amide formation in an inert solvent, followed by;
contacting the complex thus formed with N,O-dimethylhydroxylamine in the presence of a tertiary base;
d) contacting the (S)-2-(dibenzylamino)-N-methoxy-N-methylpentanamide thus formed with a reducing agent;
e) contacting the (S)-2-(dibenzylamino)pentanal thus formed with cyclopropylisocyanide in the presence of acetic acid in an inert solvent;
f) contacting the (2S,3S)-3-(dibenzylamino)-2-acetoxyhexanamide derivative thus formed with a base in an aqueous solvent;
g) contacting the (2S,3S)—N-cyclopropyl-3-(dibenzylamino)-2-hydroxyhexanamide thus formed with hydrogen in the presence of a suitable catalyst.

17. The process of claim 16, wherein in step a) the bases are a mixture of sodium hydroxide and potassium carbonate, and the benzyl halide is benzyl chloride or benzyl bromide.

18. The process of claim 16, wherein in step b) the base is sodium hydroxide, and the inert solvent is aqueous methanol.

19. The process of claim 16, wherein in step c) the reagents suitable for amide formation are 1-ethyl-3-(3'-dimethylaminopropyl)-carbodiimide and 1-hydroxybenzotriazole, the inert solvent is dichloromethane, and the tertiary base is N-methylmorpholine.

20. The process of claim 16, wherein in step d) the reducing agent is lithium aluminum hydride, and the reaction is carried out in tetrahydrofuran.

21. The process of claim 16, wherein in step e) the inert solvent is methylene chloride.

22. The process of claim 16, wherein in step f) the base is aqueous sodium hydroxide and the aqueous solvent is methanol.

23. The process of claim 16, wherein in step g) the catalyst is palladium(II) hydroxide, and the reaction is carried out in methanol or ethanol.

24. A compound of the formula:

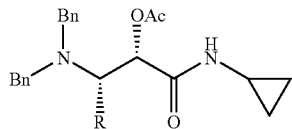

wherein R is alkyl of 1-6 carbon atoms optionally substituted by cycloalkyl of 3-6 carbon atoms and Bn is benzyl.

25. The compound of claim 24, in which R is ethyl, n-propyl, or cyclobutylmethyl, namely:
- (2S,3S)-1-(cyclopropylamino)-3-(dibenzylamino)-1-oxopentan-2-yl acetate;
- (2S,3S)-1-(cyclopropylamino)-3-(dibenzylamino)-1-oxohexan-2-yl acetate; and
- (2S,3S)-4-cyclobutyl-1-(cyclopropylamino)-3-(dibenzylamino)-1-oxobutan-2-yl acetate.

26. A compound of the formula:

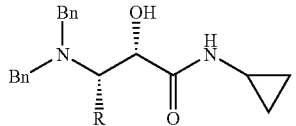

wherein R is alkyl of 1-6 carbon atoms optionally substituted by cycloalkyl of 3-6 carbon atoms and Bn is benzyl.

27. The compound of claim 26, in which R is ethyl, n-propyl, or cyclobutylmethyl, namely:
- (2S,3S)—N-cyclopropyl-3-(dibenzylamino)-2-hydroxypentanamide;
- (2S,3S)—N-cyclopropyl-3-(dibenzylamino)-2-hydroxyhexanamide; and
- (2S,3S)-4-cyclobutyl-N-cyclopropyl-3-(dibenzylamino)-2-hydroxybutanamide.

* * * * *